United States Patent [19]

Page, Jr. et al.

[11] 4,149,315
[45] Apr. 17, 1979

[54] DENTAL SYRINGE

[75] Inventors: Joe W. Page, Jr., Huntington Beach; Rod J. Koutnik, Thousand Oaks, both of Calif.

[73] Assignee: Den-Tal-Ez Mfg. Co., Des Moines, Iowa

[21] Appl. No.: 768,034

[22] Filed: Feb. 14, 1977

[51] Int. Cl.² ............................................. A61C 17/02
[52] U.S. Cl. ........................................ 32/22; 128/224; 222/571
[58] Field of Search ..................... 32/22; 128/224, 240, 128/173.1, 274; 251/79, 80, 121, 8; 138/43, 45; 222/571

[56] References Cited

U.S. PATENT DOCUMENTS

| 2,029,734 | 2/1936 | Meitzler | 128/224 |
| 2,180,702 | 11/1939 | Berwick et al. | 222/571 |
| 2,366,424 | 1/1945 | Perry | 251/8 |
| 2,791,239 | 5/1957 | Mason | 138/45 |
| 3,401,691 | 9/1968 | Beu | 128/173.1 |
| 3,506,002 | 4/1970 | Maurer et al. | 128/173.1 |
| 3,511,235 | 5/1970 | Stram | 128/173.1 |
| 3,874,083 | 4/1975 | Buckley | 32/22 |

FOREIGN PATENT DOCUMENTS

| 1491710 | 5/1969 | Fed. Rep. of Germany | 128/224 |
| 941332 | 11/1963 | United Kingdom | 128/224 |

Primary Examiner—Louis G. Mancene
Assistant Examiner—John J. Wilson
Attorney, Agent, or Firm—Rudolph L. Lowell

[57] ABSTRACT

A dental syringe is connectible to sources of air and water under pressure for selectively providing a solid stream of water, a jet of air or a spray of water and air. The maximum rate flow of air and/or water to be used is independently metered in the handle portion of the syringe to limit the flow as required by the dental work being performed. Valve assemblies in the valve body porton of the syringe for independently controlling the air and water flow have respective actuator means each of which is interconnected with the valve assembly therefor to pull back into the water passage system downstream of the valve assembly any wafter that may be adjacent to the orifice of the syringe when the water flow is interrupted.

1 Claim, 11 Drawing Figures

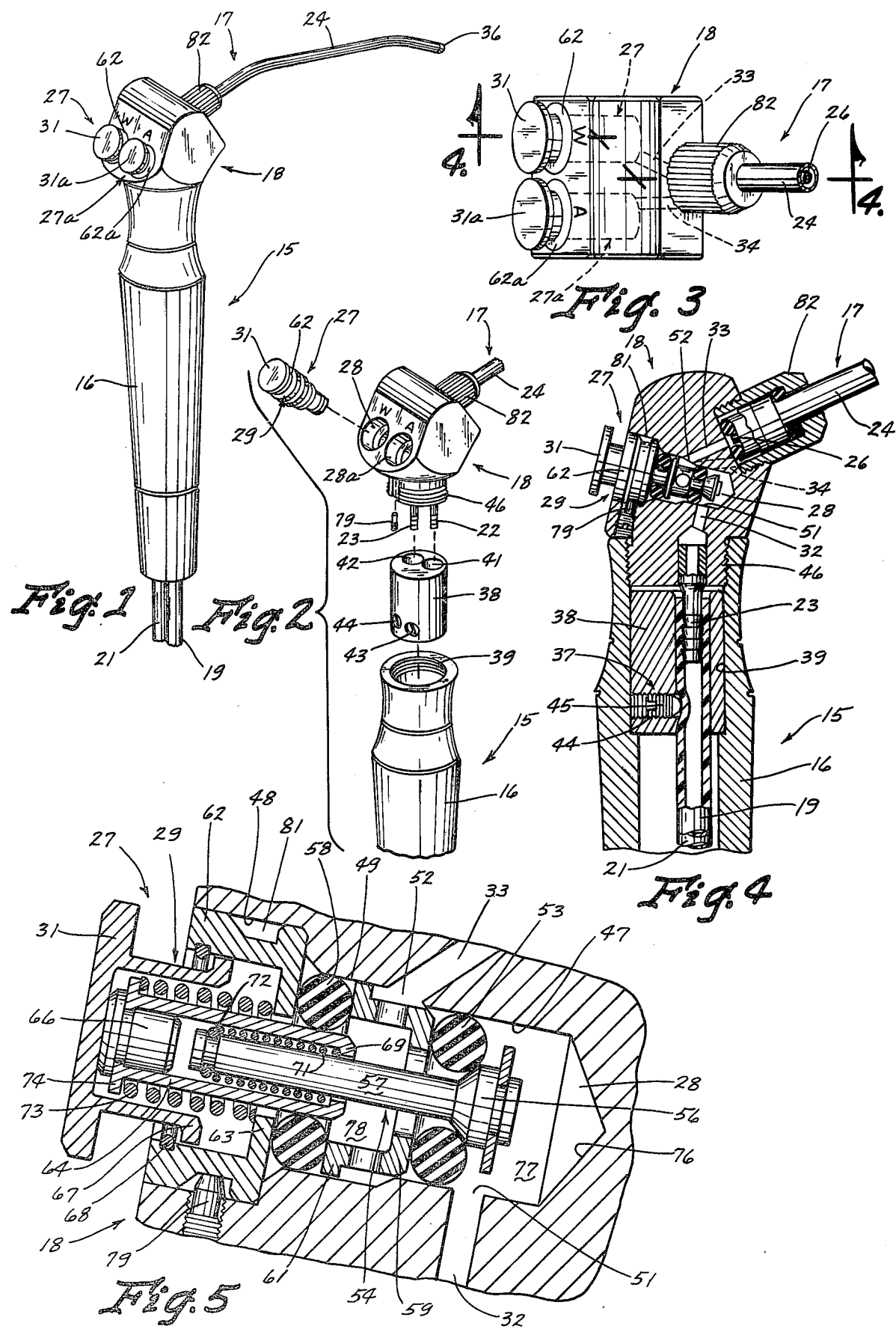

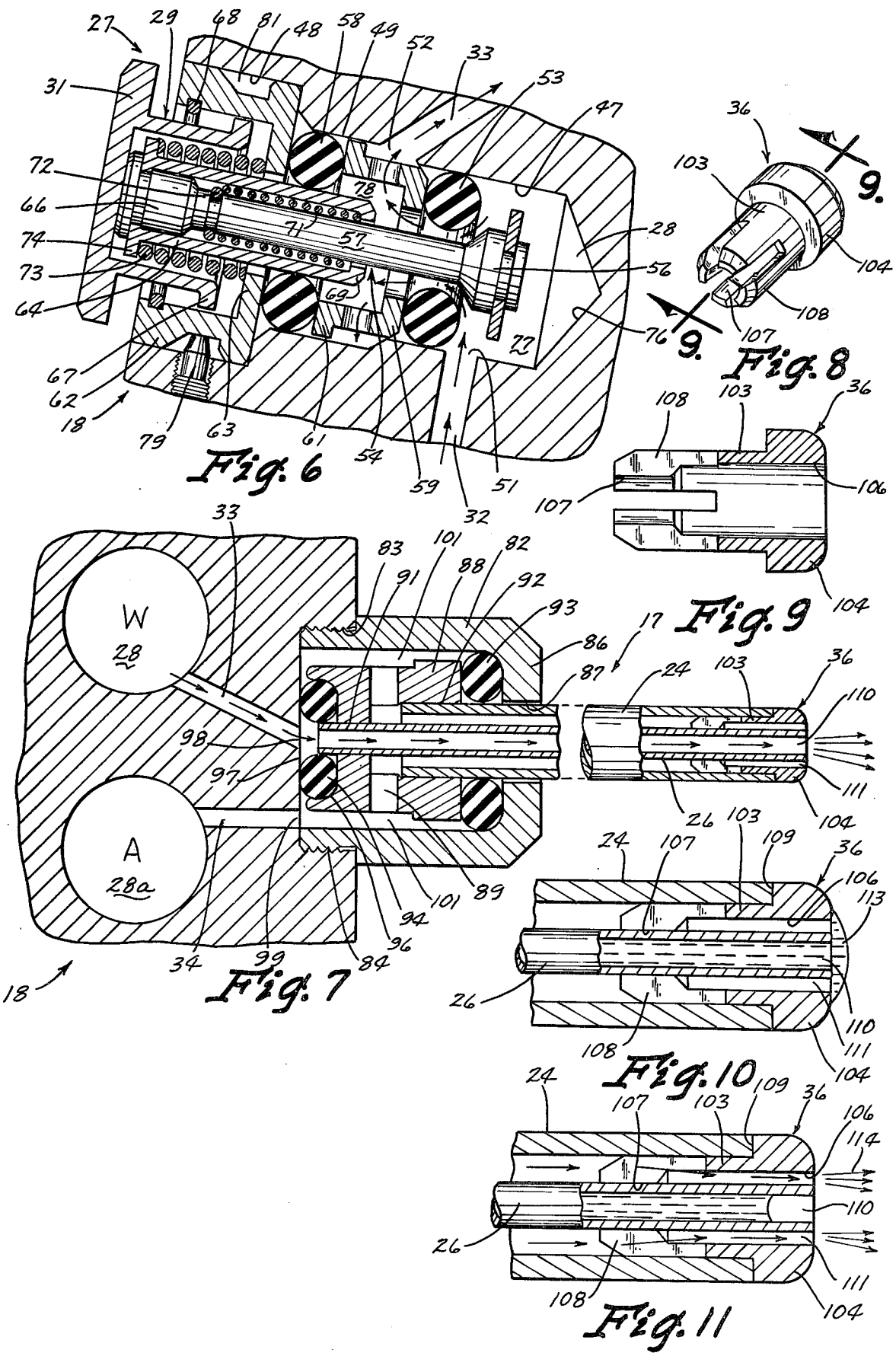

DENTAL SYRINGE

SUMMARY OF THE INVENTION

The invention provides a dental syringe having a handle portion, a valve body portion and a tip portion rotatably supported on the valve body portion to an adjusted position. A modular button-actuated valve assembly for each fluid passage system controls the "on" and "off" flow functions of the syringe. A metering valve in the handle portion upstream from a respective valve assembly is adjustable to limit the maximum rate flow in the associated passage means or system while maintaining the effectiveness of the fluid stream. A valve assembly includes a valve member that is movable to a seated position in part by the fluid pressure in a passage means so as to require a reduced spring force for closing and, in turn, a reduced operator force for opening. The interconnection of the valve assembly and actuator means therefor to provide a negative pressure at the liquid discharge orifice of the syringe, when the liquid flow is interrupted, permits the liquid and air discharge ports to be located in a common plane or surface of the discharge nozzle. A valve assembly is constructed as a module unit for convenient assembly and maintenance purposes and the metering valves in the handle portion are easily accessible. The syringe is thus readily manipulated and adjusted so as to quickly and efficiently meet the work requirements of a dentist.

BRIEF DESCRIPTION OF THE DRAWINGS

FIG. 1 is a perspective view of the syringe of this invention;

FIG. 2 is a fragmentary exploded perspective view of the syringe showing the air and liquid control valve assemblies and their respective metering valves;

FIG. 3 is an enlarged top plan view of the syringe with the tip portion foreshortened;

FIG. 4 is a fragmentary longitudinal sectional view of the syringe as seen along the line 4—4 in FIG. 3;

FIG. 5 is an enlarged longitudinal sectional view of a modular valve assembly illustrated in the closed position therefor;

FIG. 6 is illustrated similarly to FIG. 5 and shows a valve assembly in the open position therefor;

FIG. 7 is an enlarged sectional detail view showing the assembly of the tip portion with the valve body portion of the syringe;

FIG. 8 is a perspective view of a tip or cap member for the free end of the syringe tip portion;

FIG. 9 is an enlarged longitudinal sectional view of the cap member of FIG. 8;

FIG. 10 is an enlarged showing of the free end of the tip portion, shown in FIG. 7, showing a water globule that may form at the liquid discharge orifice when the water flow is interrupted; and FIG. 11 is illustrated similarly to FIG. 10, showing the pull back of the water globule of FIG. 10, as a result of the negative back pressure effected in the valve assembly on interruption of the water flow.

DETAILED DESCRIPTION OF THE INVENTION

Referring to FIG. 1 there is shown a three-way dental syringe 15 which is comprised of a hand portion 16 and a tip portion 17 interconnected by a valve body portion 18. The handle portion is of a hollow tubular construction formed to be conveniently gripped in the hand of a user. A pair of flexible tubes or hoses 19 and 21 extend through the hollow handle 16 and are connected to barbs 22 and 23 (FIG. 2) on the valve body portion 18. The tube 19 is connected to a source of air under pressure (not shown) and the tube 21 is connected to a source of water under pressure (not shown).

The tip portion 17 of the syringe 15 (FIG. 7) is comprised of a pair of rigid coaxial tubes which are mounted at one end on the valve body portion 18 and extend generally transversely of the axis of the hollow handle portion 16. The outer tube 24 of the coaxial tubes of the tip portion 17 provides a conduit section for air under pressure and the inner coaxial tube 26 a conduit section for water under pressure.

As shown in FIGS. 3 and 4, a valve assembly or mechanism 27 is installed in a cavity 28 in the valve body portion 18 and includes an actuator means 29 that has a control button 31 projecting from the valve body portion 18. Passageways 32 and 33 formed in the valve body 18 communicate with the cavity 28 at longitudinally spaced ports 52 and 51, respectively, and interconnect the inner water tube 26 of the tip portion 17 with the barb 23 and liquid hose 21 through the cavity 28 to form a continuous water passage means between the ends of which the valve mechanism 27 is interposed. Referring to FIGS. 2 and 3, it will be seen that a second valve mechanism, indicated as 27a, is installed in a second cavity 28a of the valve body 18 with the control button 31a thereof projecting from the valve body at a position adjacent the control button 31. Appropriate passageways formed in the valve body 18 and communicating with the second cavity 28a interconnects the outer conduit section 24 of the tip portion 17 with the barb 22 through the second cavity 28a to form a second continuous passage means with the valve mechanism 27a interposed between the ends thereof. This second passage means constitutes the air passage system in the syringe 15, the air to which is introduced through the air hose 19 and through the valve assembly 27a and into the tip portion 17 through a passageway indicated at 34 in FIG. 4.

In use the handle portion 16 (FIG. 1) of the syringe 15 may be held in the palm of a dentist's hand, with the tip portion 17 pointing away much in the manner of gripping a pistol. The thumb of the hand is conveniently positioned to operate either one or both of the actuator buttons 31 and 31a which project outwardly from the valve body portion 18.

When the button 31 is depressed, a solid stream of water is projected from the nozzle head 36 at the free end of the tip portion 17. Likewise, when the button 31a is depressed, a jet of air will be projected from the nozzle head 36. Since both of the control buttons 31 and 31a are located adjacent to each other, a dentist may press both buttons simultaneously in which case both water and air will be projected or discharged from the nozzle head 36 in the form of a spray. To control the maximum rate flow of fluid from the nozzle head 36, each of the fluid passage means is provided with a metering valve. The metering valve for the liquid passage means is indicated generally at 37 in FIG. 4, it being understood that the air passage means is provided with a similar metering valve (not shown). Since the valve assemblies and metering valves are carried in a dual manner within the hollow handle portion 16 and valve body 18, respectively, and are identical in construction and operation, only the metering valve and valve assembly for the liquid passage means will be described in detail with like parts in the air passage means being indicated with like numbers bearing the suffix a.

The metering valves (FIGS. 2 and 4) include a cylindrical bushing 38 fitted within a bore 39 of reduced diameter formed in the upper end of the hollow handle portion 16. The bushing is formed with a pair of adjacent longitudinally extended holes 41 and 42 for receiving the air hose 19 and liquid hose 21, respectively. Extended transversely of the bushing 38 for registration with corresponding ones of the longitudinally extended holes 41 and 42 are a pair of tapped holes 43 and 44. The hoses 19 and 21 are extended through their associated holes 41 and 42, respectively, in the bushing 38 for connection with associated barbs 23 and 22, also respectively, with the holes 41 and 42 being of a size to receive the barb connections therein.

With further reference to FIGS. 2 and 4, it is seen that the valve body portion 18 is formed with an externally threaded reduced neck section 46 for reception in and threaded connection with an internally threaded portion of the bore 39. To adjust the metering valve 37, the valve body portion 18 is disconnected from the handle portion 16 and the bushing 38 with the hoses 19 and 21 therein removed from the bore 39 to provide access to adjustment screws 45 received in the tapped holes 43 and 44 for direct engagement with the hoses. On movement of the adjustment screws 45 of the metering valve 37 inwardly of the tapped hole 44, a side portion of the hose 21 is deflected or squeezed inwardly to adjustably collapse the cross sectional area of the hose. At all adjusted positions therefor the adjustment screws 45 are within the confines of the bushing 38. On completion of the rate flow metering adjustment, the bushing 38 is replaced within the bore 39 and the valve body and handle connected together at the coacting threaded portions thereof. The maximum rate flow in a fluid passage means is thus adjusted upstream from a corresponding valve assembly 27 or 27a.

As shown for the valve assembly 27, the cavity 28 therefor (FIGS. 4 and 5) is of a cylindrical shape having an inner bore section 47 of small diameter, an outer bore section 48 of a large diameter and a central bore section 49 of an intermediate diameter. The valve assembly 27 (FIG. 5) includes a seat member comprised of an O-ring 53 extended transversely of the inner bore section 47 and in engagement with the side wall thereof at a position intermediate the ports 51 and 52. Coacting with the valve seat 53 is a valve member 54 having a head member 56 and a stem member 57. The valve head 56 is located within the inner bore section 47 with the stem member 57 projected through the valve seat and the central bore section 49 and into the outer bore section 48. Interposed between the seat 53 and an O-ring 58, extended transversely of the central bore section 49 at its junction with the outer bore section 48, is a tubular spool or spacer member 59 having an outer diameter slightly less than the diameter of the inner bore section 47. The end of the spacer member 59 adjacent the O-ring 58 is formed with a bearing portion 61 for guided engagement with the side wall of the central bore section 49.

Mounted within the outer bore section 48 is a tubular retaining bushing 62 formed at its inner end with an inwardly extended annular flange 63 for bearing engagement with the O-ring 58. Movable within the retainer bushing 62 for movement axially of the valve stem member 54 is a tubular or liquid displacement sleeve member 64. When the valve assembly 27 is in the closed position therefor of FIG. 5, the outer end of the sleeve member projects outwardly from the cavity 28 and its inner end inwardly into the central bore section 49. The projected outer end of the sleeve 64 is covered by the button 31 which is engageable with a plug 66 inserted in the outer end of the sleeve member 64. The inner end of the button 31 is formed with an outwardly extended annular flange 67 for bearing engagement with the side wall of the outer bore section 48. A snap ring 68 in the retaining bushing 62 limits the outward movement of the button 31 and in turn the outward movement of the sleeve member 64 when the valve assembly 27 is in the closed position therefor.

The sleeve member 64 is mounted about the valve stem member 57 in liquid sealed engagement with the O-ring 58 and is formed at the inner end thereof with an inwardly extended annular shoulder 69. A coil spring 71 within the sleeve member 64 is mounted about the valve stem member 54 and placed in compression between the sleeve shoulder 69 and a snap ring 72 carried at the free end of the stem member 57. A second coil spring 73, mounted about the sleeve member 64 within the outer bore section 48, is arranged in compression between the flange 63 on the retaining bushing 62 and a shoulder 74 formed at the outer end of the sleeve 64.

The springs 71 and 73 are of a relative strength such that the spring 73 exerts a compressive force greater than the compressive force of the spring 71. As shown in FIG. 5, for a closed position of the valve assembly 27, the outer end of the sleeve member 64 is in a spaced axial relation with the free end of the valve stem member 57 to provide a lost motion connection therebetween on initial depression of the button 31. Thus, the button, when initially depressed, is axially moved relative to the valve member 54 until abutting engagement takes place between the plug 66 in the outer end of the sleeve member 64 and the free end of the valve stem member 57. This initial movement of the button 31 takes place against the action of the spring 73 as reduced by an extension of the spring 71. However, such extension is without effect in unseating the valve head 56 due to the pressure of the liquid in the inner bore section 47 acting to hold the valve head 56 seated. Following the engagement of the valve stem member 57 and sleeve member 64, the continued depression of the button 31 unseats the valve head 56 to permit a flow of water under pressure from the port 51 (FIG. 6), into the inner bore section 48 and through the valve seat 53 and port 52 into the passage 33 for discharge from the nozzle head 36.

On a release of the push button 31, the valve head 56 is moved against the seat 53 by the sole action of the spring 71 to interrupt the flow of water between the cavity ports 51 and 52. With the valve head seated, the movement of the sleeve 64 is continued by the action of the spring 73 until the shoulder 67 on the button 31 is engaged by the snap ring 68.

By virtue of the projection of the sleeve member 64 within the central bore section 49, when the button 31 is fully depressed, the delayed retraction of the sleeve member outwardly from such central bore section, after seating of the valve head 56, creates a negative pressure within the passage 33 tending to pull back or withdraw water from the passage 33 into the central bore section 49.

Stated otherwise, that portion of the cavity 28 between the O-ring 53 and the cavity bottom wall 76 defines what may be called a water receiving chamber 77 and the cavity portion between the O-rings 53 and 58 a water discharge cavity 78. When the valve head 56 is in the unseated position of FIG. 6, the liquid volume of the chamber 78 is reduced by an amount corresponding to the liquid therein displaced by the extension of the sleeve member 64 therein. On a seating of the valve head 56, prior to the retraction of the sleeve 64, the subsequent retraction of the sleeve member increases the volume of the discharge chamber 78. The volume of water pulled back into the discharge chamber 78 from the passage means 33 is thus equal to the volume displacement therein by the sleeve member 64.

It will also be noted that when the valve member 54 is retained in the closed position therefor by the spring 71, and the button 31 locked within the retaining bushing 62 by the snap ring 68, the complete valve assembly 27 constitutes a module assembly which is removable from and placed within the cavity 28 as a unit package. The valve assemblies 27 and 27a (FIGS. 2 and 4) are locked against removal from their associated cavities 28 and 28a by a single lock screw 79 threadable within the valve body 18 at a position between the retaining bushings 62 and 62a for reception within a peripheral grove 81 formed in each of the bushings 62 and 62a. As clearly shown in FIG. 4, the screw 79 is accessible on disconnection of the valve body 18 from the handle 16.

The valve body 18 and tip portion 17 are assembled by means including a tubular connector member 82 (FIG. 7) having a threaded neck section 83 of a reduced diameter for threaded reception within a threaded cavity 84 formed in the valve body 18. The outer end of the connector member 82 is formed with an inwardly extended annular clamping or retaining flange 86 which defines a central opening 87. Arranged in a concentrically spaced relation within the tubular connector 82, is a cylindrical spool 88 having axially aligned bores 91 and 92.

The water conduit section 26 at the base or inner end of the tip portion 17 projects axially outwardly from the air conduit section 24 (FIG. 7). In the assembly of the tip portion with the spool member 88, the water conduit section 26 is received within the bore 91 of reduced diameter and the air conduit section 24 within the bore 92. A diametric passage 89 is in registration with the bore 92 so that fluid passing therethrough is permitted to flow about that portion of the water conduit section 26 which intersects the passage 89.

A first O-ring 93 is positioned about the air conduit section 24 between the spool 88 and the retaining flange 86 on the connection member 82. A second O-ring 94 is positioned in a seat 96 extended about the inner end of the water conduit section 26. The outlet port 98 of the discharge passage 33 from the valve assembly 27 is arranged centrally of the bottom wall 97 of the cavity 84 in axial alignment with the water conduit section 26. The outlet port 99 of the air passage 34 from the valve assembly 27a is located in the cavity bottom wall 97 adjacent the periphery thereof for communication with the annular passage 101 formed between the spool 88 and the side wall of the connector 82.

As a result of the relative arrangement of the port 98 with the water conduit section 26 and the air port 99 with the inner peripheral surface of the connector 82, the threaded engagement of the connector 82 within the cavity 84 effects a clamping of the O-ring 94 between the cavity bottom wall 97 and spool 88 concurrently with the clamping of the O-ring 93 to close the annular air passage 101 at the flange end of the connector 82. On loosening of the connector member 82 the tip portion 17 is rotatable relative to the valve body 18 to a desired adjusted position. At any adjusted position of the tip portion 17, the O-ring 94 functions to separate the water flow from the air flow at the cavity bottom wall 97 so that water from the passage 33 travels directly into the water conduit section 26 for discharge from the nozzle head 36. The air from the passage 34 is directed into the annular passage 101 and through the diametric opening 89 for travel within the air conduit section 24 and about the water conduit section 26 for discharge at the nozzle head 36.

The nozzle head 36 (FIGS. 8 and 9) is of a tubular construction and is formed with a shank 103 and a head 104. The nozzle head has an enlarged bore section 106 and a reduced bore section 107 with the side wall of the bore section 107 being slotted to provide air distributing wings 108. With the shank 103 inserted within the space formed between the coaxial conduit sections 24 and 26 until the head 104 engages the terminal face 109 of the air conduit section 24, the air flowing about the water conduit section 26 is dispersed by the wings 108 for uniform distribution about the water discharge orifice 110 of the nozzle head 36. The terminal end of the water conduit section 26 projects outwardly from the terminal face 109 of the air conduit section 24 a distance such that when the nozzle head 36 is assembled, the orifice 110 and the concentrically arranged annular air discharge port 111 are arranged in a common plane or surface of the nozzle head.

As illustrated in FIG. 10, when the water flow through the water conduit section 26 is interrupted by closing of the valve assembly 27, a globule of water, indicated at 113, may form on the nozzle 36 in a covering relation with the orifice 110 and port 111. If the air system is then actuated the globule 113 can be picked up in the jet of air issuing from the port 111. This condition is eliminated by the previously described pull back action of the sleeve member 64 relative to the water discharge chamber 78 on interruption of water flow by the valve assembly 27. As a result, and as shown in FIG. 11, the globule 113 is withdrawn back into the water conduit section 26 so that when the air system is actuated the jet of dry air, indicated by the arrows 114, is discharged without any water being present at the orifice 110. It is seen, therefore, that the extent of the sleeve projection within the water discharge chamber 78 need only be such as to withdraw the amount of water necessary to insure the issuance of the dry jet of air following an interruption of water flow.

Although the invention has been described with respect to a preferred embodiment thereof, it is to be understood that it is not to be so limited since changes and modifications can be made therein which are within the full intended scope of this invention as defined by the appended claims.

We claim:
1. A dental syringe including:
   (a) a handle portion and a tip portion interconnected by a valve body portion,
   (b) a liquid passage means extending through said syringe having a discharge orifice at the free end of said tip portion,
   (c) said valve body portion formed with a valve assembly receiving cavity interposed in said passage means having a liquid inlet and a liquid outlet,
   (d) a valve assembly having a valve seat intermediate said inlet and outlet, said cavity having a liquid receiving chamber and a liquid discharge chamber at opposite sides of said valve seat, (e) a valve member including a valve head in said liquid receiving chamber and a stem member projected through said valve seat into said liquid discharge chamber, (f) bias means for urging said valve head against said valve seat, (g) manual actuating means extending into said cavity in axial alignment with said stem member having a liquid displacement member movable into said liquid discharge chamber on actuation thereof, (h) means for yieldably urging said actuating means to an axially moved position out of engagement with said stem member when the valve head is in a seated position with said valve seat, whereby said actuating means is movable relative to said stem member prior to engagement therewith to move said valve head out of the seated position therefor, (i) said valve head, on release of said actuating means, being movable by said bias means to the seated position therefor prior to the movement of the actuating means to the axially moved position therefor, whereby any liquid at the discharge orifice of said passage means is withdrawn into said passage means by the retractive movement of said displacement member from said liquid discharge chamber, (j) said displacement member of the actuating means being tubular and mounted in a concentrically spaced relation about said stem member and formed with an inwardly projected flange at the end thereof adjacent said liquid discharge chamber, (k) said bias means comprised of a coil spring mounted about said stem member and maintained in compression between said flange and the free end of the stem member, and (l) said coil spring, on release of the actuating means, and movement of the valve head to the seated position therefor, being compressible by the actuating means on movement thereof by the yieldable means to the axially moved position therefor.

* * * * *